US005933357A

United States Patent [19]
Tipler

[11] Patent Number: 5,933,357
[45] Date of Patent: Aug. 3, 1999

[54] BACKFLUSHING SYSTEM FOR GAS CHROMATOGRAPHY

[75] Inventor: Andrew Tipler, Trumbull, Conn.

[73] Assignee: The Perkin-Elmer Corporation, Norwalk, Conn.

[21] Appl. No.: 08/851,789

[22] Filed: May 6, 1997

Related U.S. Application Data

[60] Provisional application No. 60/026,030, Sep. 13, 1996.

[51] Int. Cl.[6] .................................................. G06F 17/00
[52] U.S. Cl. ...................................... 364/528.08; 210/635
[58] Field of Search ......................... 364/528.08; 95/87, 95/88; 210/635; 73/863.11

[56] References Cited

U.S. PATENT DOCUMENTS

| | | | |
|---|---|---|---|
| 4,734,107 | 3/1988 | Trestianu | 95/87 |
| 4,960,444 | 10/1990 | Ghaoui | 95/88 |
| 5,109,710 | 5/1992 | Newkirk et al. | 73/863.11 |
| 5,242,471 | 9/1993 | Markham et al. | 95/87 |

FOREIGN PATENT DOCUMENTS 0247929  12/1987  European Pat. Off. .

OTHER PUBLICATIONS

Muto Hiroyuki, Setting Method of Back Flash Time, Nov. 1992, Patent Abstracts of Japan, Public. #06148158/5/27/94.
Michael Akard & Richard Sacks, Analytical Chemistry, vol. 66, No. 19, Oct. 1, 1994, pp. 3036–3041; Pressure–Tunable Selectivity for High–Speed Gas Chromatography.
T. Hevesi & J. Krupcik, Use of chromatographic models for computerized optimization of coupling–point pressure in dual–column gas chromatography; Journal of Chromatography, Sep. 26, 1990, Amsterdam, NL, pp. 161–173.

*Primary Examiner*—Paul P. Gordon
*Assistant Examiner*—McDieunel Marc
*Attorney, Agent, or Firm*—David Aker

[57] ABSTRACT

A method where the relationship between the observed retention time and the applied carrier gas pressure can be fitted to an expected theoretical relationship and thus enable the retention time on just the precolumn to be precisely derived. This method, used in conjunction with a dual column gas chromatography system having a precolumn, a separation column and programmable pneumatic controls to enable the inlet and midpoint pressures of the system to be independently adjusted, facilitates the use of dual-column backflush techniques without the need for a second detector or for any replumbing in order to connect the first column directly to the detector.

4 Claims, 2 Drawing Sheets

BACKFLUSHING SYSTEM FOR GAS CHROMATOGRAPHY

This invention claims priority from the Provisional Patent Application Ser. No. 60/026,030 filed on Sep. 13, 1996.

FIELD OF THE INVENTION

This invention generally relates to a backflushing system for removing unwanted material from a gas chromatography (GC) column configuration and to establishing the retention times of components eluting from the first column in a serially connected, dual column system.

BACKGROUND OF THE INVENTION

Backflushing of a capillary column to remove unwanted, less volatile material from the column after the peaks of interest have eluted is a particularly powerful technique and offers significant benefits in reducing analysis time and protecting the column in many applications. The main problem with the existing approach is that there is little control over what portion of the sample enters the column following injection. It is quite possible that heavy sample material may enter a highly retentive column and require extensive temperature programming of the column to enable efficient removal by backflushing. It is possible to minimize the amount of heavy material entering the column by using a programmable temperature vaporizer, enabling sample injection to occur at modest temperatures and allowing the less volatile sample residue to vaporize from the stationary phase during the column backflush step. While this approach has achieved demonstrable success, it does add another level of complexity to the method, the 'cut-off' between the target analytes and undesirable less-volatile sample components is not exact, the time taken to cool the injector liner adds to the analytical cycle time and the peak shape of early-eluting sample components may be compromised by matrix-retention effects at the low injection temperature.

A much better way of limiting the ingress of low volatility sample material into a highly retentive separation column is to use a pre-column which may be backflushed in series with the separation column. The use of two, serial columns in this manner mitigates many of the problems associated with backflushing a single column system. The sample is introduced into the pre-column where a crude separation between the light and heavy sample components is performed. The light components elute from the pre-column first and enter the separation column where they are further chromatographed. Once the last component of interest has eluted from the pre-column, the pre-column can be backflushed to remove the heavy material. The advantage of this approach is that the pre-column can be much less retentive than the separation column and heavy material may be backflushed much more effectively.

One of the main problems with the dual-column backflush configuration is that it is difficult to establish the optimum backflush point. Because there is no means of monitoring the peak elution between the columns, it is difficult to establish when all the peaks of interest have passed from the pre-column into the separation column. This time is critical for efficient backflushing. Various methods that have been used over the years include: 1) Running the chromatogram with the precolumn connected directly to the detector. This is not very convenient, and because the pressures will be different from when the backflush is configured, the retention times will not be very accurate. 2) Replacing the separation column with a low dead time restrictor. This is better because it enables the same pressures to be applied as in the backflush method, but is still inconvenient because the process must be repeated each time the GC backflush conditions are changed. 3) Using a monitor detector. This requires additional hardware to split the precolumn effluent. Some of the sample will be lost and an additional detector is required. Despite these disadvantages, it does offer a convenient way of establishing the backflush point.

SUMMARY OF THE INVENTION

This invention teaches a method of definitively establishing the retention times of components eluting from the pre-column in order to determine the optimum backflush point. The relationship between the observed retention time and the applied carrier gas pressure can be fitted to a calculated relationship and thus enable the retention time on just the precolumn to be precisely derived. The system is used to produce a number of chromatograms using different pressures across the precolumn but keeping the pressure across the separation column unchanged. The resultant chromatograms can be processed to predict the chromatogram eluting from just the precolumn.

The invention further discloses the method as utilized in a gas chromatograph having a dual column backflush configuration with programmable pneumatic controls. The controls enable the inlet and midpoint pressures of the system to be independently adjusted and together with the method allow the system to backflush in an automated manner.

DETAILED DESCRIPTION OF THE INVENTION

Figure 1:
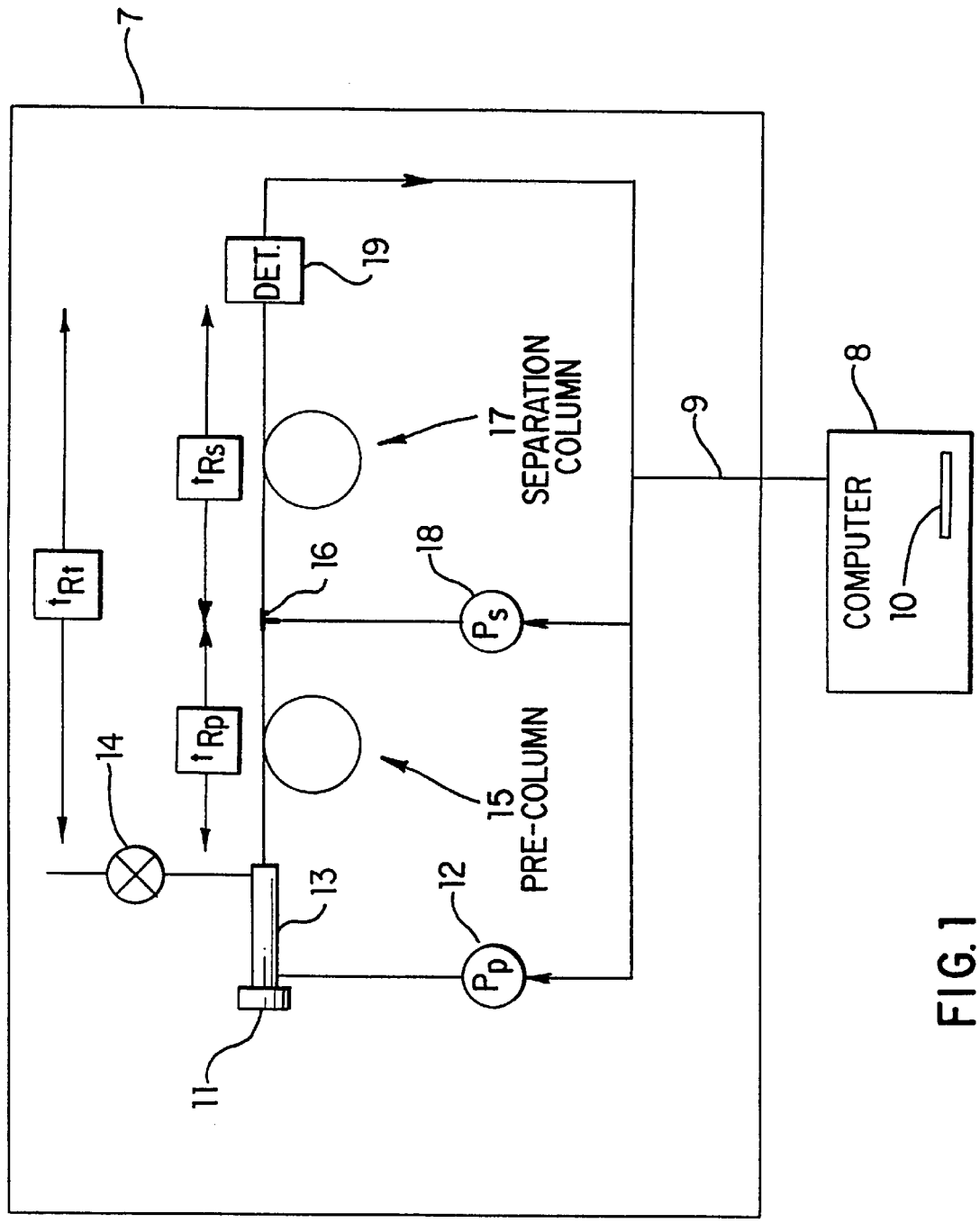
FIG. 1 is a schematic of a computer controlled dual column configuration utilizing the invention.

FIG. 1 illustrates a dual column GC system 7. The system 7 includes a split injector 11 for injecting liquid samples. A carrier gas is supplied at a first pressure determined by a controlled pressure source 12. The split injector 11 vents some of the injected gas to the atmosphere through a split valve 14.

The output of the split injector 11 is connected to a precolumn 15 which is in turn connected through a T connector 16 to a separation column 17. Connector 16 has its midpoint connected to a second midpoint controlled pressure source 18. The output of separation column 17 is provided to a GC detector 19 such as a flame ionization, thermal conductivity, mass spec or electron capture type.

A computer 8 is connected to the GC system 7 via a bus 9, to receive signals from detector 19 and to provide control signals to pressure sources 12 and 18. Suitable A/D or D/A converters (not shown) may be used. The computer 8 operates with a computer readable medium, such as a disk 10, which stores a program for performing the method described below.

The isothermal retention time of a chromatographic peak is related to the inlet and outlet gas pressures applied across the column. A chromatograph with programmable pneumatic controls enables the inlet and midpoint pressures on a dual-column backflush system to be independently adjusted. This ability enables the generation of chromatograms where only the chromatography in the precolumn is affected. The relationship between the observed retention time and the applied carrier gas pressure can be fitted to a calculated relationship, enabling the retention time on just the precolumn to be derived.

The isothermal retention time of a component, $t_R$, is related to the peak retention factor, k, according to Equation 1.

$$k = \frac{(t_R - t_0)}{t_0} \quad [1]$$

Where $t_0$ is the unretained peak time k is related to the partition coefficient, K, according to Equation 2.

$$k = K/\beta \quad [2]$$

Where $\beta$ is the stationary phase ratio $\beta$ is constant for a given column and, under isothermal conditions, K is constant—therefore k also will be constant. Equation 1 may be rearranged to give Equation 3:

$$t_R = t_0 \cdot (1+k) \quad [3]$$

Thus:

$$t_R \propto t_0 \quad [4]$$

$t_0$ is related to the column geometry, gas viscosity and gas pressures according to Pouseille's relationship given in Equation 5:

$$t_0 = \frac{4 \cdot L^2 \cdot (P^3 - 1) \cdot 32 \cdot \eta}{3 \cdot p_o \cdot (P^2 - 1)^2 \cdot d_c^2} \quad [5]$$

Where $\eta$ is the gas viscosity

P is the ratio $p/p_o$ $p_i$ is the absolute inlet pressure $p_o$ is the absolute outlet pressure L is the column length $d_c$ is the column internal diameter and absolute pressure equals gauge pressure plus ambient pressure Equation 5 uses one particular model for gas compressibility, "j" from A. T. James and A. J. P. Martin, *Biochem. J.* 50, 679–690 (1952). There may be others which yield similar results but the approach remains the same.

For a given column, temperature and carrier gas, Equation 5 can be reduced to Equation 6:

$$t_0 \propto \frac{(P^3 - 1)}{p_o \cdot (P^2 - 1)^2} \quad [6]$$

Combining Equation 4 with Equation 6 gives Equation 7:

$$t_R = \frac{c \cdot (P^3 - 1)}{p_o \cdot (P^2 - 1)^2} \quad [7]$$

Where c is a constant

If c can be calculated for a given peak, then its retention time can be determined for any combination of inlet and outlet pressures, on the same column at the same temperature. Referring to the system in FIG. 1, if the retention time of a component on the precolumn is $t_{Rp}$ and the retention time on the separation column is $t_{Rs}$ then the total retention time, $t_{Rt}$ observed at the detector will be as shown in Equation 8:

$$t_{Rt} = t_{Rp} + t_{Rs} \quad [8]$$

If the component is chromatographed twice with a different injector pressure ($P_p$) each time but keeping the midpoint pressure ($P_s$) constant, then Equations 9 and 10 are obtained:

$$t_{Rt1} = t_{Rp1} + t_{Rs} \quad [9]$$

$$t_{Rt2} = t_{Rp2} + t_{Rs} \quad [10]$$

Note that the retention time on the separation column, $t_{Rs}$, remains the same in each instance.

Equations 9 and 10 may be combined to give Equation 11:

$$(t_{Rt1} - t_{Rt2}) = (t_{Rp1} - t_{Rp2}) \quad [11]$$

Equation 11 can be combined with Equation 7 to give Equations 12 and 13:

$$(t_{Rp1} - t_{Rp2}) = \frac{c_p}{p_s} \cdot \left\{ \frac{(P_1^3 - 1)}{(P_1^2 - 1)^2} - \frac{(P_2^3 - 1)}{(P_2^2 - 1)^2} \right\} \quad [12]$$

$$(t_{Rt1} - t_{Rt2}) = \frac{c_p}{p_s} \cdot \left\{ \frac{(P_1^3 - 1)}{(P_1^2 - 1)^2} - \frac{(P_2^3 - 1)}{(P_2^2 - 1)^2} \right\} \quad [13]$$

Where:

$P_1$ is the ratio $p_{p1}/p_s$ $P_2$ is the ratio $p_{p2}/p_s$ $P_{p1}$ is the absolute pressure at the precolumn inlet for the first run $P_{p2}$ is the absolute pressure at the precolumn inlet for the second run $P_s$ is the absolute pressure at the separation column inlet (and precolumn outlet)

$t_{Rt1}$ is the total retention time through both columns for the first run $t_{Rt2}$ is the total retention time through both columns for the second run $c_p$ is the column constant (see Equation 7) for the precolumn As all the other parameters in Equation 13 can be measured experimentally, the calculation of the column constant for the precolumn, $c_p$, is now possible. Once known, this result can be entered into Equation 7 to predict the retention time at the midpoint.

The backflush point may now be established by running the sample at two different inlet pressures, locating the last peak of interest, calculating $c_p$ from Equation 13 for that component, calculating its predicted retention time on the precolumn under the applied conditions using Equation 7 and offsetting the backflush time based on the peak width, experimental error or other factors.

This approach assumes isothermal chromatography, at least during this process. Many backflush applications are isothermal. This process may also be used during an initial isothermal period, followed by temperature programming.

In order to facilitate the computations required to determine the elution times, this method may be performed by a computer program stored on a disk 10, inserted into computer 8.

Figure 2:
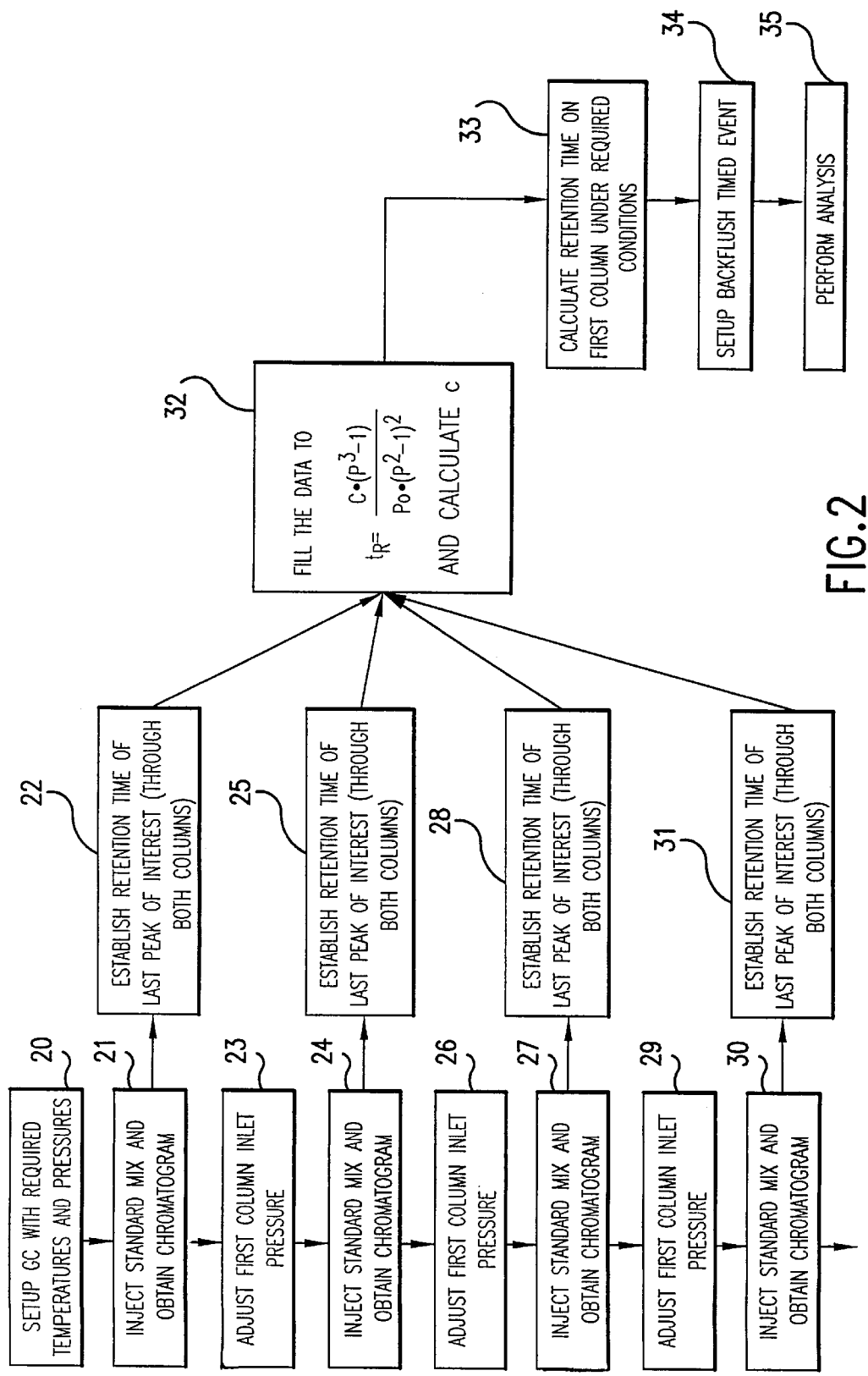
FIG. 2 is a flow chart of an embodiment of the method according to the invention.

FIG. 2 illustrates the method of determining the retention time of component of interest using a series of data points. While the flowchart shows collecting four or more data points, a minimum of two data points is required to perform the method. An operator sets up a gas chromatograph with the desired temperatures and pressures in step 20. A standard mix containing analytes of interest is injected and a chromatogram is obtained in step 21. The retention time of the last analyte of interest is measured through both columns in step 22. The inlet pressure at the first column (the precolumn) is changed to a new value in step 23 and the standard mix is injected again under this new pressure and a new chromatogram is obtained in step 24. The retention time of the last analyte of interest is measured for the second time. The inlet pressure at the first column is adjusted to a third value in step 26. The standard mix is again injected and another chromatogram is obtained under this new pressure in step 27 and the retention time of the last analyte of interest is measured a third time in step 28. The inlet pressure at the column is adjusted for a fourth time in step 29. The standard mix is again injected and a new chromatogram is obtained in step 30 and the retention time of the last analyte of interest is measured for a fourth time in step 31. The process of adjusting the first column inlet pressure, injecting the standard mix, obtaining the related chromatogram and measuring the retention time of the analyte of interest may be repeated as many times as desired but only two iterations are required for this method. The collected retention time data is then used in the equation below:

The data is fit to $$t_R = \frac{c \cdot (P^3 - 1)}{p_o \cdot (P^2 - 1)^2}$$

and the column constant, c, is calculated in step 32. The retention time of the last analyte of interest through the first column is then calculated in step 33. Using that retention time, the backflush event can then be set up on the gas chromatograph in step 34 and conventional analysis performed in step 35.

We claim:

1. In a gas chromatography column system including
   an injector having an input and an output, said input configured to allow introduction of samples into said injector, said injector constructed to allow samples to vaporize and travel through said injector from said input to said output;
   a first pressure control means attached to said injector for controlling the pressure of said gas chromatography column system;
   a precolumn comprising a gas chromatography column having an input and an output said input connected to said injector and configured to receive said sample from said injector output, said precolumn constructed to allow said sample to travel through said precolumn from said precolumn input to said precolumn output, said precolumn constructed to separate components of said sample such that some components elute from said precolumn output side at different times than other components of said sample;
   a separation column having an input and an output, said separation column constructed to allow sample to pass from said input, through said column to said output, said separation column further constructed to cause components of said sample to elute from the output side of said separation column at different times;
   a connection between said precolumn output and said separation column input, said connection configured to allow samples to pass from said precolumn output to said separation column input;
   a second pressure control means attached to said connection for controlling the pressure at said connection; and
   a detector attached to said separation column output for detecting said components of said sample;
   a method for backflushing said gas chromatography column system comprising:
   setting said first pressure control means to apply a first desired pressure value;
   setting said second pressure control means to a selected pressure value, said selected pressure value being selected to allow chromatography to occur through said chromatography column system;
   injecting a first sample of a standard containing analytes of interest into said injector;
   measuring the retention time of the last component of interest of said first sample in said gas chromatography column system;
   setting said first pressure control means to apply a second desired pressure value;
   injecting a second sample of said standard into said injector;
   measuring the ambient pressure;
   measuring the retention time of the last component of interest of said second sample in said gas chromatography column system; and
   calculating the retention time of said component of interest through said precolumn as a function of said first desired pressure value, said second desired pressure value, said selected pressure value, said retention time of said last component of interest of said first sample, said retention time of said last component of interest of said second sample and said ambient pressure.

2. The method of claim 1 wherein the system further includes a computer and a computer usable medium, having computer readable program code means embodied therein for causing said computer to perform a series of steps, further comprising using the computer to at least partially perform the steps of:
   setting said first pressure control means to apply a first desired pressure value;
   setting said second pressure control means to a selected pressure value, said selected pressure value being selected to allow chromatography to occur through said chromatography column system;
   controlling the injection of a first sample of a standard containing analytes of interest into said injector;
   measuring the retention time of the last component of interest of said first sample in said gas chromatography column system;
   setting said first pressure control means to apply a second desired pressure value;
   controlling the injection of a second sample of said standard into said injector;
   measuring the ambient pressure;
   measuring the retention time of the last component of interest of said second sample in said gas chromatography column system; and
   calculating the retention time of said component of interest through said precolumn as a function of said first desired pressure value, said second desired pressure value, said selected pressure value, said retention time of said last component of interest of said first sample, said retention time of said last component of interest of said second sample and said ambient pressure.

3. In a gas chromatography column system including
   an injector having an input and an output, said input configured to allow introduction of samples into said injector, said injector constructed to allow samples to vaporize and travel through said injector from said input to said output;
   a first pressure control means attached to said injector for controlling the pressure of said gas chromatography column system;
   a precolumn comprising a gas chromatography column having an input and an output said input connected to said injector and configured to receive said sample from said injector output, said precolumn constructed to allow said sample to travel through said precolumn from said precolumn input to said precolumn output, said precolumn constructed to separate components of said sample such that some components elute from said precolumn output side at different times than other components of said sample;

a separation column having an input and an output, said separation column constructed to allow sample to pass from said input, through said column to said output, said separation column further constructed to cause components of said sample to elute from the output side of said separation column at different times;

a connection between said precolumn output and said separation column input, said connection configured to allow samples to pass from said precolumn output to said separation column input;

a second pressure control means attached to said connection for controlling the pressure at said connection; and a detector attached to said separation column output for detecting said components of said sample;

an article of manufacture comprising:

computer readable program code, stored on a computer usable medium and executable by a data processing system, for backflushing a gas chromatography column system, the code comprising:

means for setting said first pressure control means to apply a first desired pressure value;

means for setting said second pressure control means to a selected pressure value, said selected pressure value being selected to allow chromatography to occur through said chromatography column system;

means for controlling the injection of a first sample of a standard containing analytes of interest into said injector;

means for measuring the retention time of the last component of interest of said first sample in said gas chromatography column system;

means for setting said first pressure control means to apply a second desired pressure value;

means for controlling the injection of a second sample of said standard into said injector;

means for measuring the ambient pressure;

means for measuring the retention time of the last component of interest of said second sample in said gas chromatography column system; and means for calculating the retention time of said component of interest through said precolumn as a function of said first desired pressure value, said second desired pressure value, said selected pressure value, said retention time of said last component of interest of said first sample, said retention time of said last component of interest of said second sample and said ambient pressure.

4. In a gas chromatography column system including an injector having an input and an output, said input configured to allow introduction of samples into said injector, said injector constructed to allow samples to vaporize and travel through said injector from said input to said output;

a first pressure control means attached to said injector for controlling the pressure of said gas chromatography column system;

a precolumn comprising a gas chromatography column having an input and an output said input connected to said injector and configured to receive said sample from said injector output, said precolumn constructed to allow said sample to travel through said precolumn from said precolumn input to said precolumn output, said precolumn constructed to separate components of said sample such that some components elute from said precolumn output side at different times than other components of said sample;

a separation column having an input and an output, said separation column constructed to allow sample to pass from said input, through said column to said output, said separation column further constructed to cause components of said sample to elute from the output side of said separation column at different times;

a connection between said precolumn output and said separation column input, said connection configured to allow samples to pass from said precolumn output to said separation column input;

a second pressure control means attached to said connection for controlling the pressure at said connection; and a detector attached to said separation column output for detecting said components of said sample;

a computer program product comprising:

a computer usable medium having computer readable program code, stored on a computer usable medium and executable by a data processing system, for backflushing a gas chromatography column system, the code comprising:

computer readable program code means for causing a computer to effect setting said first pressure control means to apply a first desired pressure value;

computer readable program code means for causing a computer to effect setting said second pressure control means to a selected pressure value, said selected pressure value being selected to allow chromatography to occur through said chromatography column system;

computer readable program code means for causing a computer to effect controlling the injection of a first sample of a standard containing analytes of interest into said injector;

computer readable program code means for causing a computer to effect measuring the retention time of the last component of interest of said first sample in said gas chromatography column system;

computer readable program code means for causing a computer to effect setting said first pressure control means to apply a second desired pressure value;

computer readable program code means for causing a computer to effect controlling the injection of a second sample of said standard into said injector;

computer readable program code means for causing a computer to effect measuring the ambient pressure;

computer readable program code means for causing a computer to effect measuring the retention time of the last component of interest of said second sample in said gas chromatography column system; and computer readable program code means for causing a computer to effect calculating the retention time of said component of interest through said precolumn as a function of said first desired pressure value, said second desired pressure value, said selected pressure value, said retention time of said last component of interest of said first sample, said retention time of said last component of interest of said second sample and said ambient pressure.

* * * * *